United States Patent [19]

Fine et al.

[11] Patent Number: 5,171,533
[45] Date of Patent: Dec. 15, 1992

[54] BIOLOGICAL ASSAY CASSETTE AND METHOD FOR MAKING SAME

[76] Inventors: Richard A. Fine, 5 Eden La. W., Mercer Island, Wash. 98040; John T. Kingsley, 10022 NE. 127th Pl., C112, Kirkland, Wash. 98034; Gerald L. Klein, 3804 E. Walnut, Orange, Calif. 92669

[21] Appl. No.: 387,917

[22] Filed: Jul. 31, 1989

[51] Int. Cl.⁵ .............................. B01D 21/26
[52] U.S. Cl. .................... 422/72; 422/101; 436/45; 436/177; 435/287; 210/782; 210/789; 210/516; 210/518
[58] Field of Search .............. 422/72, 101; 436/45, 436/177; 435/287; 210/782, 789, 516, 518

[56] References Cited

U.S. PATENT DOCUMENTS

| | | | |
|---|---|---|---|
| D. 273,807 | 5/1984 | Holen | D24/56 |
| D. 273,987 | 5/1984 | Holen et al. | D24/17 |
| D. 292,230 | 10/1987 | Holen | D24/22 |
| 4,435,293 | 3/1984 | Graham, Jr. et al. | 422/101 X |
| 4,469,793 | 9/1984 | Guigan | 436/45 |

FOREIGN PATENT DOCUMENTS

| | | |
|---|---|---|
| 0160282 | 4/1985 | European Pat. Off. |
| 0160901 | 4/1985 | European Pat. Off. |
| 0160901 | 7/1989 | European Pat. Off. |

OTHER PUBLICATIONS

Brochure, Olympus "Reply", Olympus Clinical Instruments Division, 4 Nevada Drive, Lake Success, N.Y. 11042-1179, (800) 223-0125, no publication date.
Newsletter with article on "Reply", Olympus Clinical Information Digest, vol. 2, No. 1, early 1988.
Advertisement for Olympus "Reply", Olympus Corporation, Clinical Instruments Division, 4 Nevada Drive, Lake Success, N.Y. 11042-1179, no publication date.
Brochure, Kodak Ektachem Analyzers, Kodak Clinical products, Eastman-Kodak Company, Jul. 1988.
Brochure, "The Vision System", Abbott Laboratories, North Chicago, Ill. 60064, (1-800-342-5228), Mar. 1985.
Brochure, Kodak Ektachem Analyzer Support & Service, Kodak Clinical Products, Rochester, N.Y. 14650, Sep. 1987.
Brochure, The Technicon Ra-1000 System, Technicon Instruments Corporation, Feb. 1985.
Brochure, Technicon RA-1000 ISE Module, Technicon Instruments Corporation, 511 Benedict Avenue, Tarrytown, N.Y. 10591, Mar. 1984.
Brochure, Technicon Data Manager, Technicon Instruments Corporation, 511 Benedict Avenue, Tarrytown, N.Y. 10591-5097, 1984.
Brochure, Reflotron, Boehringer Mannheim Diagnostics, 9115 Hague Road, Indianapolis, Ind. 46250, 1985.
Brochure, Stratus Immunoassay System, American Hospital Supply Corporation P.O. Box 560672, Miami, Fla. 33152, 1986.
Stratus "Ferritin", American Hospital Supply Corporation, P.O. Box 560672, Miami, Fla. 33152, 1985.
Stratus Antiarrhythmic/Cardiac Glycoside Panel and Thyroid Panel, American Hospital Supply Corporation, P.O. Box 560672, Miami, Fla. 33152, 1987.
Article, "Two-Dimensional Centrifugation for Desk-Top Clinical Chemistry", Clinical Chemistry, vol. 31, No. 9, 1985.

Primary Examiner—Robert J. Warden
Assistant Examiner—Stephanie Blythe
Attorney, Agent, or Firm—Seed and Berry

[57] ABSTRACT

A modular reaction cassette has a fluid metering mechanism and valves for releasing fluid which are actuated by various centripetal acellerations generated in an automated patient analysis instrument having a variable speed rotor. Various geometries and sealant materials are used to select the rotational speed at which the sealant material yields to operate the metering device and release valves.

21 Claims, 7 Drawing Sheets

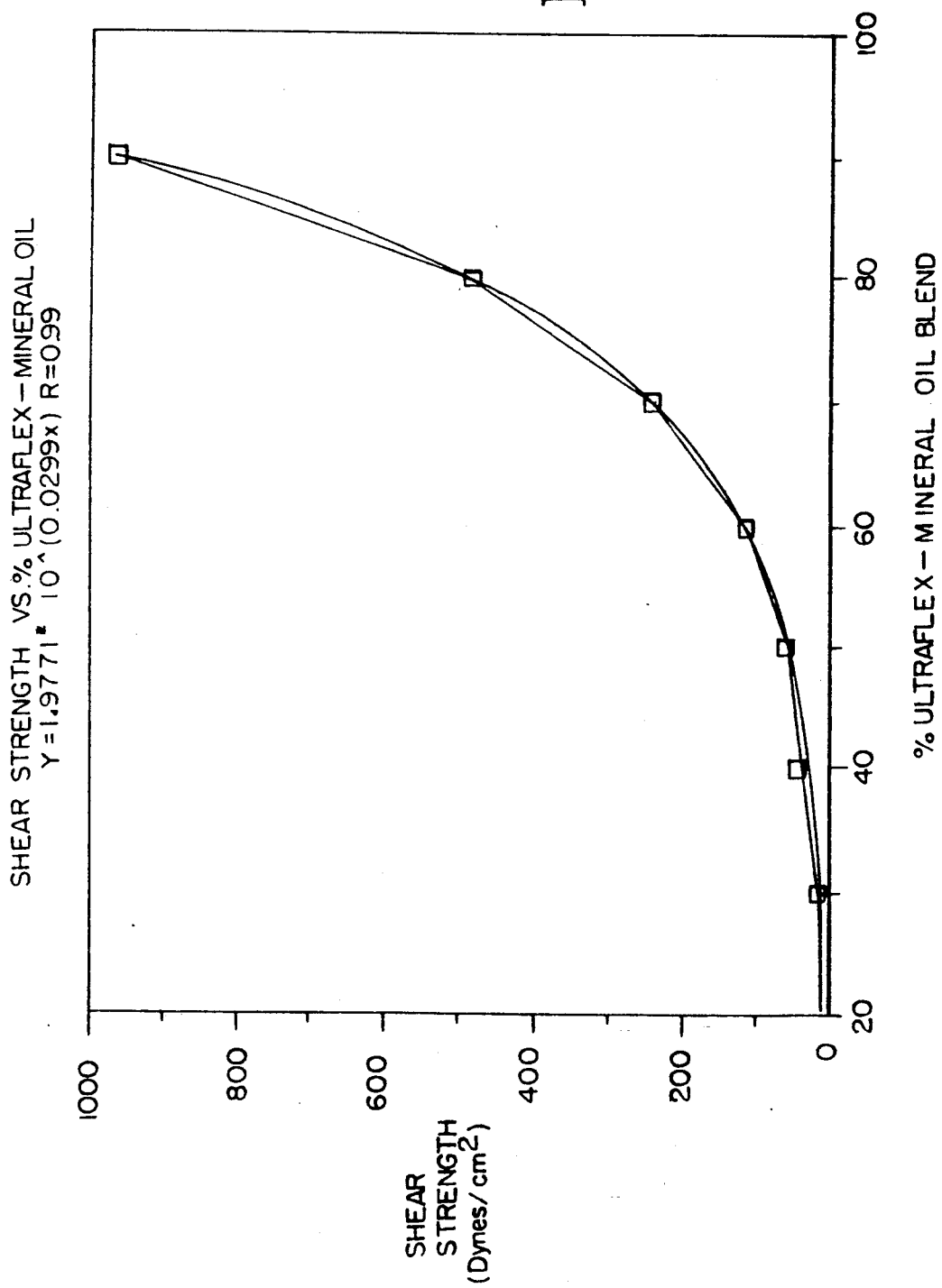

BIOLOGICAL ASSAY CASSETTE AND METHOD FOR MAKING SAME

DESCRIPTION

1. Technical Field

The invention generally relates to self-contained, biological assay apparatus. More specifically, the invention relates to self-contained cassettes or cartridges for performing biological assays, and methods for constructing such cassettes or cartridges.

2. Background of the Invention

Automated patient sample analysis devices have been developed to reduce human error in the performance of assays. Instruments of this type typically comprise apparatus used by laboratories to process hundreds of thousands of assays in a single day. These instruments are expensive and generally require the attention of a skilled technician for proper operation and to ensure reliability of assay results.

A typical instrument used in high volume test environments is a high throughput system offered by Olympus Clinical Instruments Division, under the trademark "REPLY." The "REPLY" instrument is a large system requiring approximately 7 feet by 11 feet of dedicated floor space. The "REPLY" instrument handles 400–600 tests per hour in a random access operating mode typical of moderate to high volume routine testing.

The operator of the above apparatus must prepare and replenish the reagents and monitor the apparatus' proper operation. In addition, the technician must be sufficiently competent to reconfigure the apparatus to perform different assays and various classes of assays.

Automated apparatus of the type described above have been very successful in large biological laboratories. However, such an apparatus is not satisfactory for use in physicians, offices, by untrained personnel, or for processing a small number of patient samples. For this purpose, self-contained assay cartridges have been developed which contain all of the required reagents for performing an assay.

Such a cartridge is described in European Patent Application Publication 0,160,282 filed by Abbott Laboratories. An apparatus for processing the cartridge is described in published European Patent Application No. 0,160,901, also filed by Abbott Laboratories. The cartridge described in the Abbott Laboratories applications is adapted to be processed on a centrifuge which rotates about a rotational axis. The centrifuge is provided with an axially displaced, secondary rotation axis to rotate the cartridge 90 degrees within the plane of the centrifuge. This compound, rotary motion is required to cause the reagents and patient sample to be appropriately metered and dispensed into various compartments. The cartridge is mechanically complex, and is expensive to manufacture.

The assignee of the present application has developed a mechanically simpler, self-contained assay cartridge which is shown and described in U.S. patent application Ser. No. 127 944, which was filed on Dec. 1, 1987 (now abandoned), the disclosure of which is incorporated herein by reference.

Basically, the self-contained assay cartridge utilizes a plurality of immiscible fluid layers having differing specific densities. The layers are arranged axially within the cartridge which is adapted for processing in a variable speed centrifuge. The assay cartridge also contains, at one end proximal to the centrifuge rotational axis, an internal reservoir sealed with a meltable wax plug. The internal reservoir contains a reaction component which when mixed with an incomplete reaction mixture in the cartridge forms a reagent for acting on patient sample (such as whole blood or serum). Differing specific densities of the layers prevents intermixing of the layers when the cartridge is centrifuged and agitated. The meltable plug permits mixture of the reagent with patient sample upon heating the plug. The patient sample in the end adjacent to the complete reaction mixture, after suitable incubation and agitation, is passed through these immiscible layers by centrifugal force to react therewith and to produce an optically measurable result in at least one of the layers, or at the end of the cartridge as defined by the direction of centrifugal force.

The assignee of the present invention has also invented an automated apparatus and method for processing the above-described, self-contained assay cartridges. This apparatus and processing method is described in U.S. patent application Ser. No. 07/387,916 entitled "Method and Apparatus for Measuring Specific Binding Assays" co-filed with this application, the disclosure of which is incorporated herein by reference.

Basically, the apparatus described in the assignee's co-filed application comprises a variable speed centrifuge adapted to receive a plurality of the self-contained cartridges. The centrifuge is enclosed by a lid having light sources for transmitting light through one or more of the fluid immiscible layers to detectors placed beneath the rotor of the centrifuge. These transverse detector-emitter pairs are used to perform absorption measurements through one or more of the layers. At the periphery of the rotor, a phosphorescence detector-emitter pair is located to perform phosphorescence measurements on an optical window at one end of the self-contained cartridges.

The above-described, self-contained cartridge, utilizing the immiscible fluid layers, has revolutionized assay processing for unskilled technicians. However, a need exists for a reaction cassette which allows for miscible fluid technologies, including alternative cushions, as well as the immiscible fluid technology described above but which is otherwise adapted for use with the automated analysis equipment described in the assignee's co-filed application.

In addition, the assignee's above-described immiscible fluids assay cartridge does not provide any means for metering a precise amount of patient sample into the cartridge. Certain assays require that a precise quantity of patient sample in the form of plasma separated from whole blood be introduced into the conjugation reactants to produce a photometric result which is indicative of a biological or chemical reaction occurring in the cartridge.

SUMMARY OF THE INVENTION

Therefore, it is an object of the present invention to provide a method for separating a precipitate and for metering a precise amount of fluid sample in a self-contained assay cartridge which is mechanically simple and easy to manufacture.

It is another object of the invention to achieve the above object with a cartridge which is designed to be processed by centrifugation, incubation, and agitation.

It is yet another object of the invention to achieve the above two objects without requiring the cassette to undergo a complex or compound motion during processing.

It is still yet another object of the present invention to achieve all of the above objects with a metering technique which is adaptable to a reaction cartridge which processes the metered sample in response to rotation of the automated analysis instrument's rotor.

The invention achieves these objects, and other objects and advantages which will become apparent from the description that follows, by providing a metering device which aliquots a precise amount of fluid from a metering chamber upon the application of a predetermined force or acceleration to the chamber.

In the preferred embodiment of the invention, the metering device relies on a structure utilizing a shearing seal having a predetermined shear strength. The shear strength is selected to permit a movable member to move from a first metering position, through a second sealed position to a third dispensing position upon the application of the predetermined acceleration or centrifugal force for a defined time period.

In one preferred embodiment of the invention, the metering chamber is axially connected to various combinations of reaction chambers, additional metering chamber particle washing chambers and/or photometric detection chambers for further processing and/or detection of the aliquoted sample. The cartridge is designed for automated analysis in the assignee's automated patient sample analysis instrument described in U.S. patent application Ser. No. 07/387,916 co-filed herewith.

In one of these various, preferred embodiments, the metering chamber is connected to a first reaction chamber, a second reaction chamber, and a photometric detection chamber. Each of the reaction chambers has a centrifugal force actuated release valve. The release valves permit the contents of each reaction chamber to be released into a next adjacent chamber upon the application of a second or third predetermined centrifugal force, greater than the first predetermined centrifugal force which actuates the metering mechanism in the metering chamber.

The release valves, as well as a movable member in the sample metering mechanism, utilize a sealing material having a preselected shear strength, whereby the metering member and release valves move relative to their supporting structure upon the application of the appropriate predetermined accelerations or forces. The release valves, or the metering member in the metering chamber, can also be provided with a tensile release structure which utilizes a preselected tensile strength of the sealing material to tune the releasing resistance which will permit the release valves or movable member to respond to a preselected force.

Each of the above-described seals is formed by fixing the movable member (i.e., release valve or aliquoting member) relative to the adjacent, fixed member such that a gap is formed between the movable and fixed members. The gap is then filled with melted sealant. The members and sealant are allowed to cool below the freezing point of the sealant so that the fixed and movable members are held rigid with respect to one another. The gap dimensions are selected such that the melted sealant is drawn into the gaps by capillary action and surface tension.

In one of the preferred embodiments, a particle washing/detection chamber is provided with an accumulation device for concentrating the population densities of particles entering a washing chamber. The accumulation device increases the local population density of particles at a fluid interface which is positioned in the particle washing chamber. The increased population density facilitates the movement of the particles across a fluid meniscus which forms at the fluid interface in the particle washing chamber.

BRIEF DESCRIPTION OF THE DRAWINGS

FIG. 12 is a graph of the shear strength of the sealing material versus the seal blend.

BEST MODE FOR CARRYING OUT THE INVENTION

Figure 1:
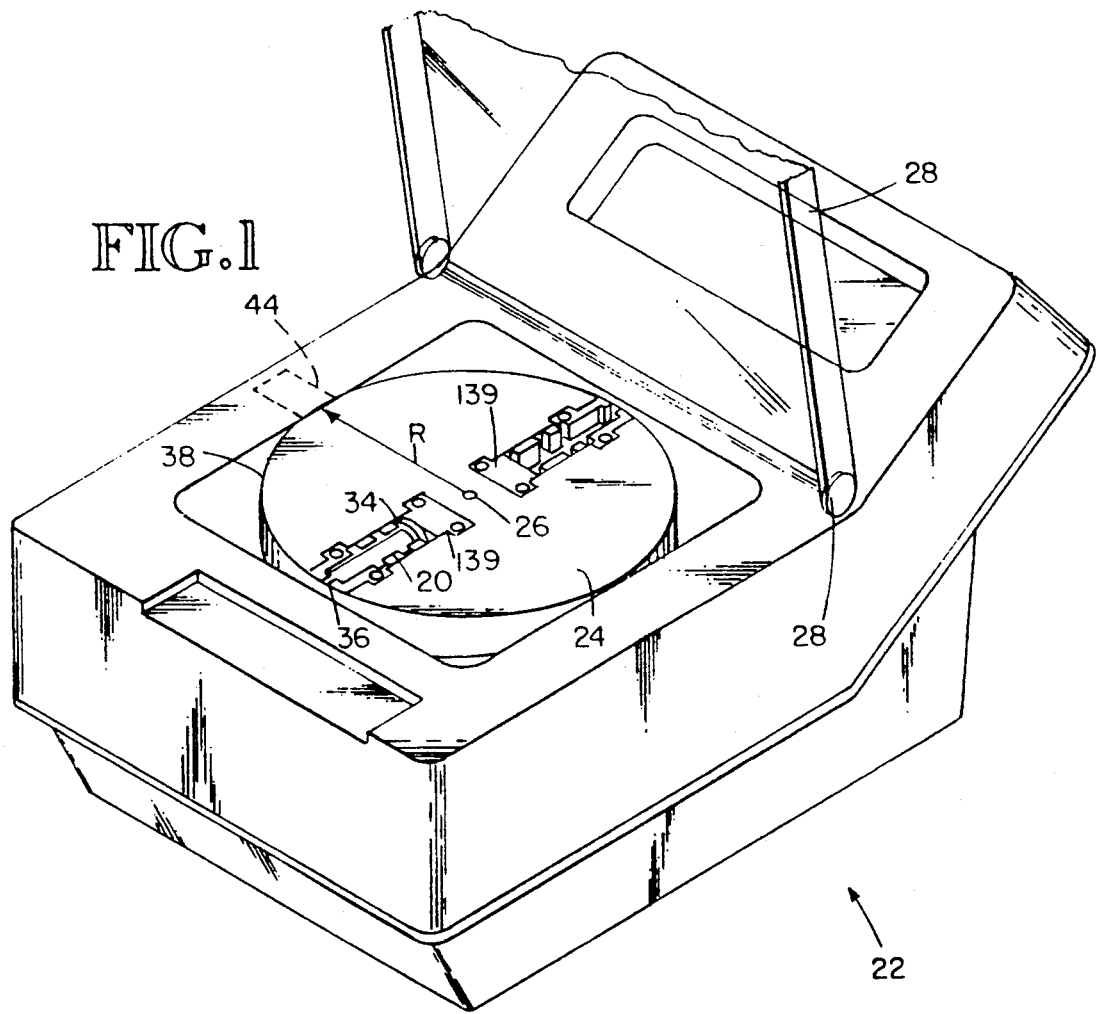
FIG. 1 is an isometric view of a reaction cartridge, in accordance with the present invention and used with an automated patient sample processing instrument as described in the assignee's U.S. patent application Ser. No. 07/387,916 entitled "Method and Apparatus for Measuring Specific Binding Assays" co-filed herewith.

A self-contained, acceleration responsive reaction cartridge, in accordance with the present invention, is generally indicated at reference No. 20 in FIG. 2A. The cartridge is adapted for processing in a fully automated analysis instrument, such as the type shown in FIG. 1 at reference No. 22 and described in co-filed U.S. patent application Ser. No. 07/387,917 "Method and Apparatus for Measuring Specific Binding Assays," assigned to the assignee of the present invention.

Overview of the Instrument

The fully automated analysis instrument 22 basically comprises a microprocessor-controlled instrument having a rotor 24 adapted to revolve around an axis 26 up to a speed of approximately 10,000 rpm. The speed of the rotor is controlled according to instructions stored in the microprocessor's memory. The rotor has a radius of approximately four inches. The instrument has a lid 28 which contains a plurality of light sources (such as lamp 30 shown in FIG. 2A) to direct interrogating light beams vertically through the cartridge 20 to a detector (such as the detector 32 shown in FIG. 2A) to perform absorbance measurements on the cartridge. Fluorescence measurements and the like are taken by an optical system 44.

The lamp 30 and detector 32 are shown in FIG. 2A in the plane of the figure. In reality, the lamp and detector exist in a plane perpendicular to the plane of the figure, and with respect to the cartridge 20 of FIG. 2A, because the lamp and detector are located in the lid 28, and beneath the rotor 24, respectively, of the instrument 22 shown in FIG. 1.

Figure 2:
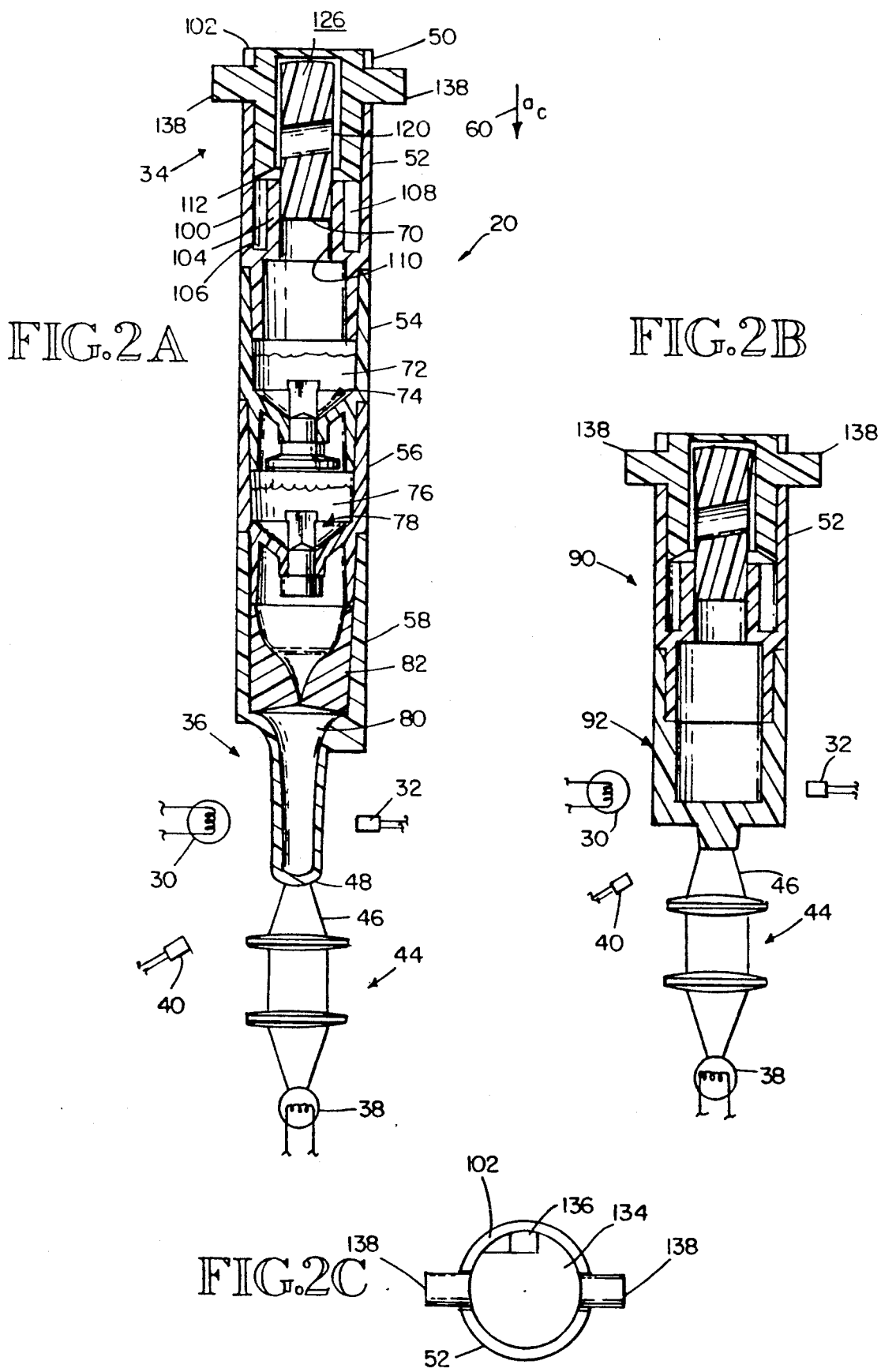
FIG. 2A is an enlarged, sectional, elevational view of the reaction cartridge shown in FIG. 1.
FIG. 2B is an enlarged, sectional view of an alternate embodiment of the reaction cartridge.
FIG. 2C is a top plan view of the reaction cartridge shown in FIGS. 2A and 2B.

The instrument 22 was designed to process self-contained assay cartridges, such as the type shown in U.S. patent application Ser. No. 07/127,944 (now abandoned) entitled "METHOD AND DEVICES FOR CONDUCTING ASSAYS". These cartridges use a plurality of immiscible fluid layers of differing density to process samples introduced at one end of the cartridge (the end located toward the axis 26 of the rotor 24) through the various layers to a distal end; such as distal end 36 adjacent to the periphery 38 of the rotor. The instrument can also process a self-contained assay cartridge of the type shown in FIGS. 2-6. At the rotor periphery, absorption measurements are taken by lamp-detector pairs 30, 32 as shown in FIG. 2A or by a fluorescence emitter 38, detector 40 pair shown in FIG. 2A. An optical system for the fluorescence-emitter detector pair 38, 40 is generally indicated at reference numeral 44 in FIG. 2A and is indicated by dotted lines in FIG. 1. The optical system focuses an interrogating light beam 46 on a curved optical window at the end 48 of the cartridge such that the interrogating beam is parallel to the radius of curvature of the end to minimize refraction and reflection of the light beam.

The rotor 24 is also capable of a compound motion which agitates cartridges received in the rotor while the rotor is spinning or at rest. A heating element (not shown) is provided beneath the rotor to incubate the cartridges. Thus, the automatic reaction-cartridge analysis instrument 22 has means for receiving a plurality of self-contained reaction cartridges, centrifuging the cartridges at various speeds, incubating the cartridges, and agitating the cartridges such that samples containing an analyte of interest entering the cartridges at one end 34 adjacent to the center of the rotor is processes axially toward the distal end 36 of the cartridge 20 for photometric analysis thereat. The entire process is controlled by the instrument 22.

Description of the Various Cartridge Preferred Embodiments

The self-contained, force-responsive reaction cartridge of the present invention is modular in construction. Each of the preferred embodiments to be described hereinbelow comprise various assemblies of the modular elements.

The first embodiment 50 is shown in FIG. 2A and comprises four modular, interconnecting sections: an aliquoting section 52, a first reactant section 54, a second reactant section 56, and a photometric analysis section 58. Each of these sections are axially interconnected so as to receive fluid from the next adjacent section, in the direction of centrifugal force indicated by arrow 60. The centrifugal force is provided by the rotor 24 of the automated analysis instrument 22, shown in FIG. 1. This first embodiment is well adapted for assays in which human blood contains the analyte of interest. The analyte could be digoxin, thyroid stimulating hormone (TSH). These assays utilize either competitive or sandwich assay technique which typically bind an enzyme conjugate. The conjugate is then exposed to a fluorogenic latex particle or other agent for subsequent photometric analysis.

In the first embodiment 50 (FIG. 2A) of the reaction cartridge 20, anticoagulated whole blood is centrifugally separated into cells and plasma. The plasma is then precisely metered by a sliding metering member 70 into the first reactant section 54 upon the application of a first, predetermined centrifugal force. The first, predetermined centrifugal force is caused by rotating the rotor 24 of the automated analysis 22 at a first, predetermined rotational speed. The first reactant section 54 contains an appropriate conjugate 72 for the analyte of interest. After an appropriate incubation and agitation cycle, the rotational speed of the rotor 24 is increased until a second, predetermined rotational speed is achieved which causes a second, predetermined centripetal force to act upon a first centrifugal force-sensitive release valve, generally indicated at reference numeral 74. The first release valve 74 permits the contents of the first reactant section 54 (i.e., the reacted mixture of the metered plasma and the conjugate) to enter the second reaction section 56. After a subsequent agitation and incubation period, the rotor 24 increases to a third, predetermined rotational speed so as to exert a third, predetermined centrifugal force on a second, force sensitive release valve, generally indicated at reference numeral 78, so as to empty the contents of the second reaction section 56 into the photometric analysis chamber 58. The structure and operation of the second release valve 78 is similar to the structure and operation of the first release valve 74.

The photometric analysis section 58 contains water immiscible washing liquid 80 and allows penetration of dense particles with bound conjugate thereunto, but excludes the bulk of liquid conjugate and reaction solution. The washing liquid 80 has a relatively high surface tension which impedes the dense particles from passing through the interface between the washing liquid and the reactant solution 78, which is juxtaposed thereto. To facilitate the penetration of particles, the photometric analysis section 58 is provided with an accumulator device 82 to increase the local population density of the particles at the washing liquid/reaction solution interface. In this manner, a relatively moderate centrifugal force can move the resulting high density population of particles through the fluid interface.

In reference to FIG. 2A, the photometric module can be assembled by adding wash liquid 80 prior to insertion of accumulator 82, then firmly inserting the accumulator. If excess wash liquid 80 is present, it may then be aspirated from the region above the accumulator. Alternatively, the accumulator 82 may be assembled in the photometric module prior to the addition of wash liquid 80. Centrifugal force can be used to cause the liquid to penetrate to the bottom 48 of the photometric module, with the expulsion of air bubbles through the orifice of the accumulator 82.

In some embodiments, the photometric module may contain two or more immiscible liquids, including wash liquid 80. Because the liquids are immiscible, they can be added to the photometric module together or in any order, using the procedures described above.

A second embodiment 90 of the reaction cartridge 20, shown in FIG. 2A, is shown in FIG. 2B. This second embodiment uses the same aliquoting section 52 as does the first embodiment. However, in the second embodiment, the reactant sections 54 and 56 of the first embodiment are not utilized, and a simplified photometric analysis section 92 is connected directly to the aliquoting section 52. This embodiment is useful for analysis of homogeneous reactions, such as calcium, glucose, cholesterol, etc., which do not involve a particle washing process. The simplified photometric analysis section 92 is adapted for fluorescence-type measurements. More commonly, absorbance-type measurements are made, using lamp 30 and detector 32.

As is apparent from the brief description of the first and second cartridge embodiments above, the modular nature of the self-contained, acceleration-responsive reaction cartridge 20 permits a variety of combinations of interfitting sections which are appropriate for a variety of different assays. All of the combinations which are and will be apparent to one of ordinary skill in this art are therefore considered to be a part of this disclosure, including structural combinations for chemistries and assays which have yet to be developed.

The aliquoting section 52 of both the first 50 and second 70 embodiments provides a structurally simple force-responsive aliquoting or metering mechanism which is precise in operation and inexpensive to manufacture. The entire reaction cartridge 20, in all its embodiments, is manufactured from a clear plastic material such as acrylic V-8-11 manufactured by Rohm and Hass. The aliquoting technique embodied in this structure only requires the application of centrifugal force which differs in magnitude and not direction. Thus, the metering of a precise amount of analyte can be achieved without complex machinery. The aliquoting section 52 is provided with a downwardly extending collar 111 having an outer diameter selected to engage in an interference fit with an upper portion of any of the remaining modular sections.

The aliquoting section 52 of the preferred embodiment includes an annular fluid metering chamber 100 having a cylindrical outer wall 102. A cylindrical inner wall 104 is connected to the outer wall 102 by a radial annulus 106 so as to form a toroidal chamber or sump 108 having an open upper end. The sliding metering member 70, previously described, has a substantially cylindrical body designed to slide within a bore 110 formed by the inner wall 104. The bore has a diameter of 0.204", which is slightly larger than the diameter 0.202" of the cylindrical body, so that an annular gap 112 of 0.0010" is formed therebetween.

Figure 3:
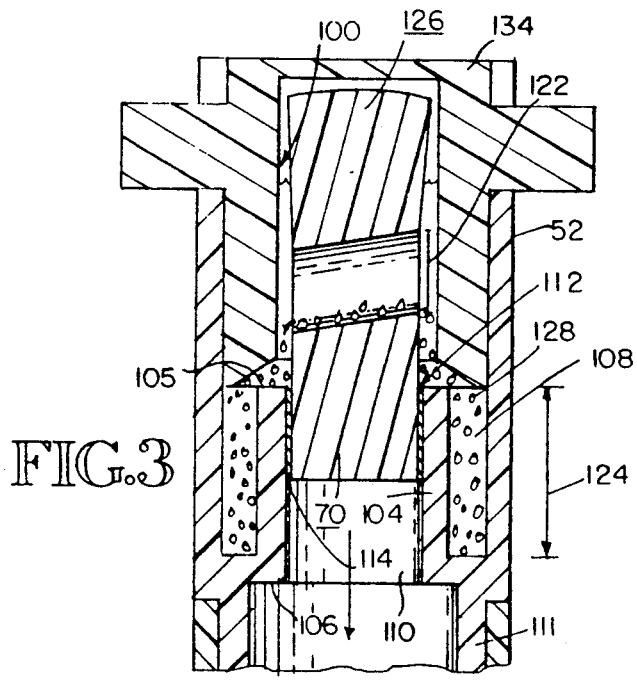
FIG. 3 is an enlarged, sectional, elevational view of a metering mechanism used with the cartridges shown in FIGS. 2A and 2B with a movable aliquoting member shown in a fluid-collection position.

A sealant, best seen in FIGS. 3 through 6A, is provided in the gap to maintain the metering member 70 in the position shown in FIGS. 2A and 3, until a first, predetermined centrifugal force is achieved. If sufficient work is done on the seal at the selected force, the metering member will move from a first fluid-collecting position shown in FIGS. 2A and 3, through a sealed position shown in FIGS. 4 and 6A, to a fluid-dispensing position shown in FIG. 5.

Figure 5:
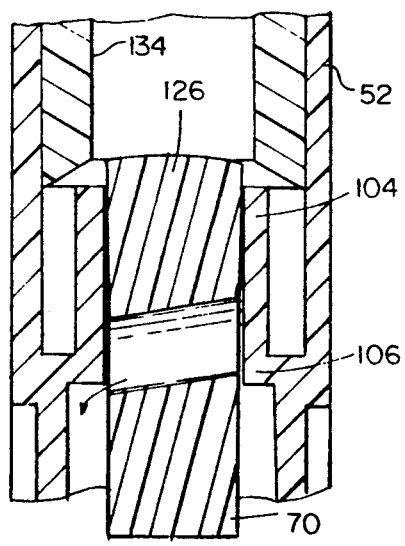
FIG. 5 is an enlarged, sectional, elevational view of the aliquoting mechanism shown in FIGS. 3 and 4 with the movable metering mechanism shown in a fluid-dispensing position.
Figure 4:
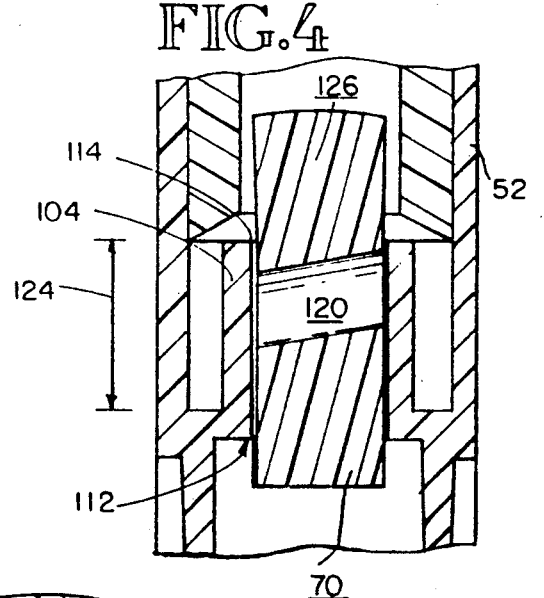
FIG. 4 is an enlarged, sectional, elevational view, similar to FIG. 3 with the aliquoting member shown in a second, sealed position under the application of a first predetermined centrifugal force.

The metering member 70 is provided with a metering cavity 120 to collect and dispense a precise quantity (50 microliters) of centrifuged patient sample from the aliquoting section 52 into a next adjacent section, connected thereto. As best seen in FIGS. 3 through 6A, the metering cavity 120 has a total height 122 (measured along the axis of the cylindrical body of the metering member) which is less than the total height 124 sealed by the inner wall 104 of the fluid metering chamber 100 and the sealant 114 in the annular gap 112. See FIG. 4. The metering member 70 is provided with an enlarged end portion 126 to limit the maximum travel of the metering member 70 as shown in FIG. 5, so that at least a portion of the metering cavity 120 is exposed beneath the radial annulus 106. In this manner, the metered fluid is dispensed into the next adjacent section as shown in FIG. 5.

The enlarged end portion 126 also serves to seal the bore 110 to prevent metered fluid from escaping therethrough into the next adjacent section and to limit the amount of superfluous material transferred with the metering member 70 from the first to the third position. To this end, the enlarged end portion has a radially outward taper of approximately 3 degrees. The upper end of the bore 110 is provided with a complimentary 3 degree radially outward taper.

The metering chamber 120 shown in FIGS. 2 through 6A comprises a transverse bore, canted at an angle of approximately twenty degrees with respect to the axis of the cylindrical body of the metering member 70. The cylindrical side wall of this transverse bore, together with the sliding member when in the sealed position shown in FIG. 4, defines a volume of approximately 50 microliters.

The slight downward cant of the transverse bore is advantageous when aliquoting plasma from a whole blood sample as best seen in FIG. 3. Whole blood contains plasma, an essentially clear fluid, and red blood cells. For various assays, it is highly desirable to separate the whole blood cells from the plasma by centrifuging the mixture. As shown in FIG. 3, under centrifugal force, the whole blood cells migrate towards the radial annulus 106 and become trapped in the toroidal chamber or sump 108 during revolution of the rotor 24. Any blood cells in the traverse bore of metering cavity 120 will tend to migrate out of the cavity, in the direction of the slope into the toroidal chamber, leaving only plasma in the metering cavity.

Figure 6A:
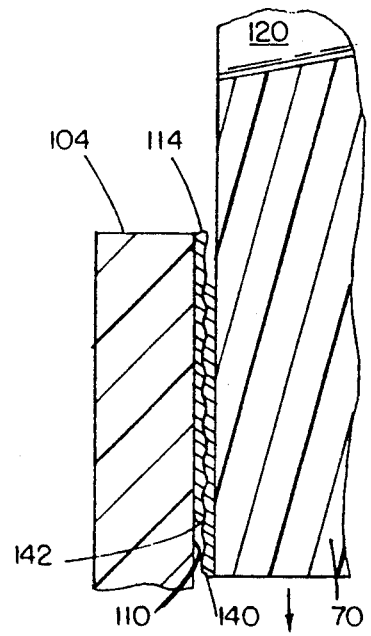
FIG. 6A is an enlarged view of the section indicated by circled area 6A in FIG. 4.
Figure 6B:
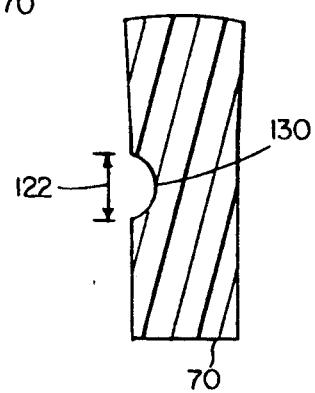
FIG. 6B is an alternate embodiment of the movable aliquoting mechanism shown in FIGS. 3 through 6A.

For applications requiring a smaller volume (approximately 5 microliters) of metered sample, the metering cavity can take the form of a hemispherical divot 130 shown in FIG. 6B. The divot can be formed in the metering member 70, provided that the height 122 of the divot is less than the total height 124 sealed by the cylindrical inner wall 104 and sealant 114. At least a portion of the divot must be exposed beneath the radial annulus 106 when the enlarged portion 126 engages the bore 110.

Figure 6C:
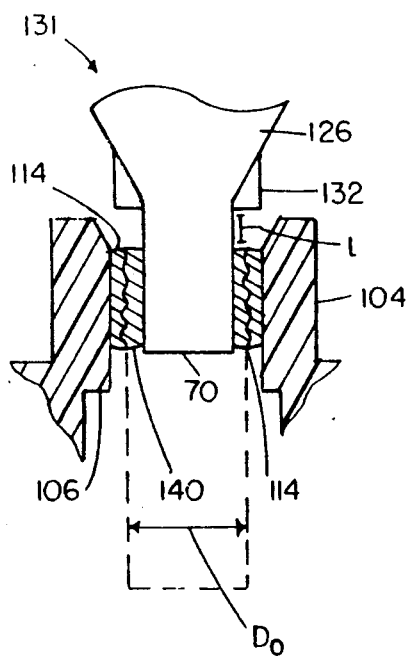
FIG. 6C shows a further alternate embodiment of the movable metering mechanism.

FIG. 6C shows an alternative metering member embodiment 131 having a circumferential shoulder 132. The circumferential shoulder has a length and a diameter selected so as to meter a volume of liquid V defined by the area between the shoulder, the seal and the fracture line of the seal according to: $V = \pi l (D_o^2 - D_i^2)/4$. The shoulder 132 can be varied in length (axially) to vary the volume V. This embodiment can be used to meter whole blood cells from plasma by eliminating the toroidal chamber 108 and selecting the length of the shoulder 132 so that 1 is less than the anticipated height of the whole blood cell volume.

As best seen in FIG. 2C, patient sample is introduced into the aliquoting section 52 through an end cap 134 by way of a flexible seal 136 on the periphery thereof. The end cap has an outer diameter selected so as to provide an interference fit with the inside of the cylindrical outer wall 102 of the fluid metering chamber 100. The end cap is provided with transverse, opposed ears which guide the reaction cartridge 20 into fixtures on the rotor 24 as seen in FIG. 1.

The selection, application and composition of the sealant 114, as well as the mass of the metering member 70 and structure of the abutting sealing surface, are extremely important to the proper and predictable operation of the aliquoting section 52 and the centrifugal sensitive release valve 74 and 78 as is described below.

In the preferred embodiment 50 shown in FIGS. 3 through 6A, the bore 110 formed by the inner wall 104 has a height of approximately 0.287" (0.729 cm) and an inner diameter of 0.204" (0.518 cm), so as to provide a sealing surface area of approximately 1.183 cm². The sliding member 70 has an outer diameter of approximately 0.202" over approximately two-thirds of its total length. The annular gap formed between the metering member 70 and the bore 110 is therefore approximately 0.0010". At least a portion of the metering chamber 120 must be exposed beyond the upper end 105 of the inner wall 104 so that the metering cavity is exposed to the metering chamber 100 which contains the fluid to be metered.

The reaction cartridge 20 is positioned on the rotor 24 such that the center of mass of the metering member is positioned approximately 1.754" from the axis of rotation 26. Upon achieving a rotational speed of 5059 rpm, the metering member 70 and aliquoted fluid contained in the metering cavity 120 (together having a mass of approximately 0.34 gm) will experience a centrifugal force of approximately 1,454 times the acceleration due to gravity (Gs) or 422,400 dynes according to the formula $F_c = mV^2/R$ where $F_c$ is the centrifugal force experienced by the metering member 70, m is the combined mass of the metering member and the metered fluid in the metering cavity 120, V is the linear velocity of the metering member, and R is the radial distance of the metering member from the axis of rotation. The sealant will shear as shown in FIG. 6A if a blend of 75% Ultraflex brand synthetic branched chain hydrocarbon polymer (available from Petrolite Corporation, Petrolite Specialty Polymers Group, 6910 East Fourteenth Street, P.O. Drawer K, Tulsa, Okla. 74112) and mineral oil (available from Squibb Corporation, P.O. Box 4,000, Princeton, N.J. 08540) is used, and if the centrifugal force is applied for an appropriate time period. This composition, and the geometry described above, will yield a shear strength of 382,000 dynes/cm² as shown in the graph in FIG. 11. The release force required to break this seal is the product of the shear strength and the sealed surface area (1.183 cm²). Shear strengths for other blends are also shown.

Figure 13:
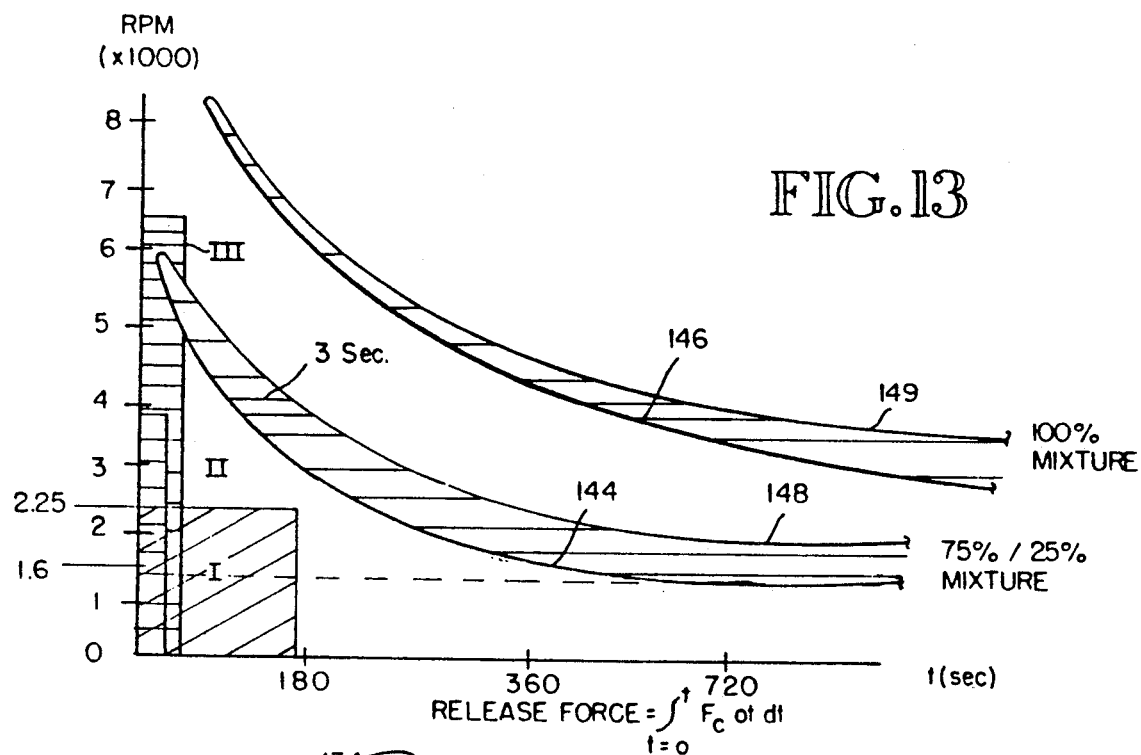
FIG. 13 is a graph of the work characteristic of the sealing material as a function of centrifugal force, time and seal blend.

The graph of shear strength shown in FIG. 11 describes the sealant material shear strength for various mixtures when an instantaneous force is applied. The actual shear characteristic of the material is a function of the plastic creep on the material. Thus, the effect of centrifugal force on the metering member 70 and release valves 74, 76 is cumulative and must be accounted for. The amount of force required to break the seal on the metering member 70 as a function of centrifugal force (rotor rpm) and time is shown in FIG. 13. In this example, the line 144 represents the minimum amount of force which must be done to break the seal according to: rupture force $= \int F_c^c \, t \, dt$. As is apparent from the graph, the line 144 approaches time axis asymptotically. Thus, the rupture force (centrifugal force applied over a time period) must be done at a centrifugal force (represented by rotor rpm) above a certain magnitude (approximately 1600 rpm). For example, during separation of plasma from whole blood, the cartridge 20 is centrifuged for 180 seconds at 2250 rpm. The amount of work done on the seal is represented by shaded area I in FIG. 13 and is insufficient to break the seal (i.e., is less than the product of applied centrifugal force, and time, indicated by the coordinates on line 144). The speed of the rotor is quickly increased to 3500 rpm to break the seal. As shown by shaded area II, the cartridge need only be subjected to rotation at the higher rpm for a few seconds for the sum of shaded areas I and II to exceed the product of the force and time coordinates at 3500 rpm indicated by line 141. Thus, for all speeds above the asymptotic value of 1600 rpm, the cartridge can be exposed to low speed rotation (i.e., to separate plasma from whole blood or to precondition the seal for a quick release) without breaking the seal if the product of the applied force (rpm in FIG. 11) and time is less than the product of the coordinates on line 144 at the same speed.

Figure 14:
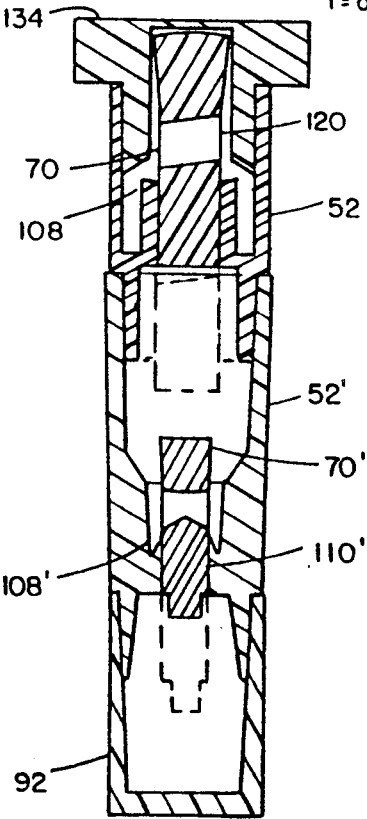
FIG. 14 is an enlarged, sectional view of a double aliquoting embodiment of the reaction cartridge.

As is apparent from the above description, the preconditioning effect of centrifuge rotation to release a first seal must be accounted for in determining the amount of work required to release each subsequent seal. For example, an HDL cholesterol test cartridge (FIG. 14) employs two aliquoting sections in series. The metering member of the first section has a 50 microliter volume while the metering member of the second section 52' has a 15 microliter volume.

The second section 52' has a metering member 70' having a mass of 0.139 gm, and a diameter of 0.134". The bore 110' has a diameter of 0.139" and a length of 0.180" so that an annular gap defining a gap distance of 0.0025" is created. A 100% Ultraflex mixture is used in the gap. The metering member 70' has a center of mass positioned approximately 7.8 cm from the rotation axis 26 so that the seal will shear when a rotational speed of 4100 rpm (1,348 Gs) is maintained for 45 seconds after the first section 70 has been centrifuged at 2250 rpm for 3 minutes and 3500 rpm for approximately three seconds. For HDL determinations, the second section is filled with a dextran-sulfate (20 micrometers). The second section is provided with an annular sump 108' to separate the sample reagent mixture from a resulting precipitate. The photometric chamber 92 is connected to the second section 42' and contains 300 microliters of cholesterol reagent.

As stated above, the second section uses a sealant mixture of 100% Ultraflex. Line 146 of FIG. 13 represents the rupture force or work required to shear the seal in the second section. To prevent premature rupture of this seal, the total amount of plastic creep induced by the process of rupturing the first seal in the first section (the sum of shaded areas I and II) must not exceed the rupture force to release the second seal. This total rupture force or work is the product of the coordinates of line 146 at 6500 RPM. To release the second seal, only the rupture force represented by shaded area III need be added to the rupture force already applied, represented by shaded areas I and II.

Use of a high speed spin of above 3000 rpm to add the final amount of rupture force necessary to shear a seal is desirable to compensate for manufacturing tolerances of the seal structure and seal composition. The areas bound by lines 144, 148 and 146, 149 represent the manufacturing variability of the seal structure. At higher rotational speeds, the work curves exhibit a manufacturing variability of approximately three seconds at a given rotational speed. At low speeds (speeds slightly above the threshold release speed of 1600 rpm for the 75%–25% mixture) the manufacturing variability is on the order of many minutes due to the asymptotic shape of the curve in the lower speed ranges.

The manner in which the sealant 144 shears is also important. As shown in FIG. 6A, the sealant tends to shear into an inner toroidal segment 140, connected to the lower portion of the sealing member 70, and an outer toroidal segment 142, connected to the bore 110. Retention of at least a portion of the seal by the bore 110 is particularly important so that the open ends of the metering chamber 120 remain sealed when the metering member 70 is in the sealed position shown in FIG. 4. In any event, different yield forces for the seal 114 can be achieved by changing the surface area of the abutting surfaces.

Description of the Release Valves

The first and second centrifugal force sensitive release valves 74 and 78 in the first and second reactant sections operate under principles similar to the metering member 70 in the aliquoting section 52.

Figure 7:
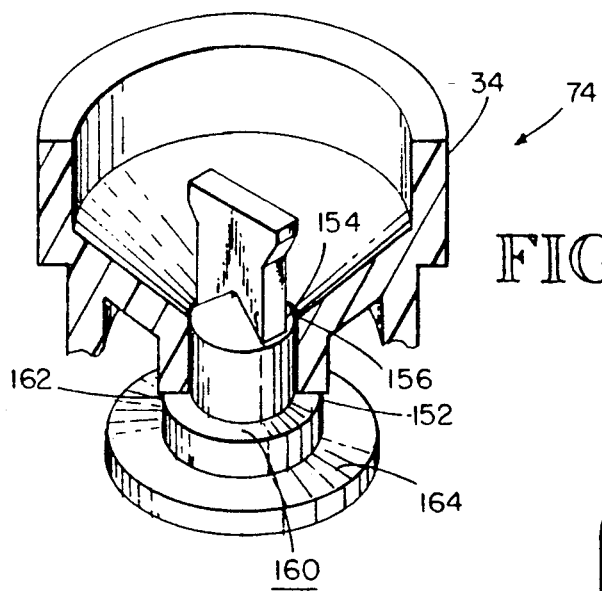
FIG. 7 is an enlarged, sectional, diametric view of a release valve shown in FIG. 2A with the release valve shown in the closed position.
Figure 8:
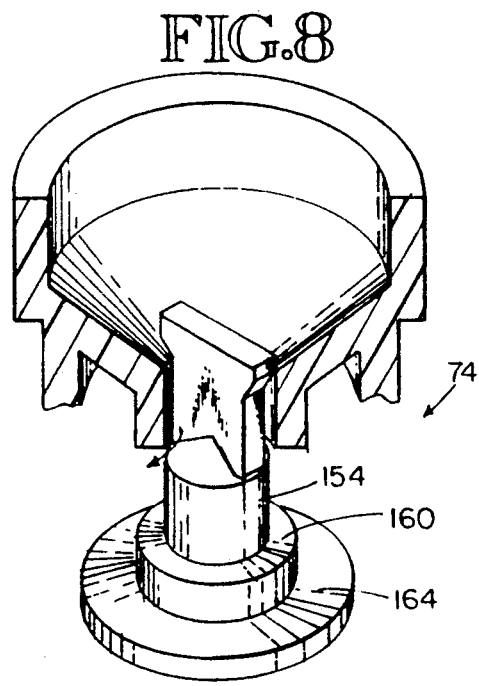
FIG. 8 is a sectional, isometric view of the release valve of FIG. 7 shown in the open position.
Figure 9:
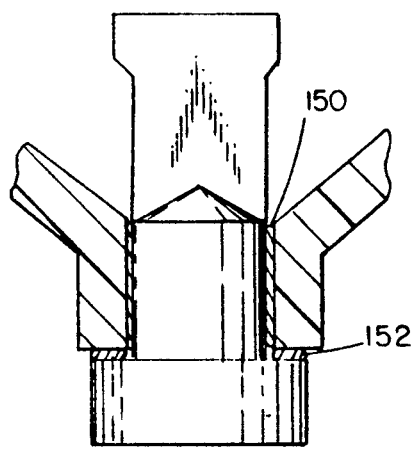
FIG. 9 is an enlarged, sectional, elevational view of the release valve of FIG. 7 illustrating the shear and tensile seals having predetermined shear and tensile strengths.

Enlarged, sectional views of the first acceleration sensitive release valve are shown in FIGS. 7 and 8, in the closed and opened positions respectively. An enlarged, sectional view showing both a shear seal 150 and a tension seal 152 are best seen in FIG. 9. The first release valve 74 has a cylindrical valve body 154 having a diameter of approximately 0.108", which is positioned in a bore 156 having a diameter of approximately 0.110". The bore 156 is in the base of the first reactant section 54. This difference in diameters forms an annular gap between the cylindrical body 154 and bore 156, having a thickness of approximately 0.002". The bore has a height of approximately 0.097" to form a sealant surface area of approximately 0.034 cm$^2$. The release valve 74 also has a foot section extending radially from the cylindrical body. The foot section provides a radial sealing surface 160 to abut against an opposed radial sealing surface 162 on the end of the side wall which forms the cylindrical bore 156. The interface between the radial sealing surfaces 160 and 162 is filled with the sealant 152. The first release valve 74 also has a peripheral skirt 164 adapted to radially disburse fluid exiting the open valve as shown in FIG. 8.

The first release valve 74 is designed to open at a second centrifugal force (achieved at approximately 6200 RPM), greater than the first centrifugal force (achieved at approximately 5,050 rpm) which actuated the metering member 70 in the aliquoting section 52. To achieve this performance, the first release valve, with the peripheral skirt, and the "head" of fluid thereabove in the first reaction section, have a combined mass of approximately 0.108 gm. Alternatively, the mass can be increased and the ratio of Ultraflex to mineral oil is selected as 83.3% to 16.5%, to yield the required release force of 622 dynes/cm$^2$. The approximate center of gravity of the valve is located 7.2 cm from the center of rotation 26 of the rotor 24 so as to provide a total centrifugal force of 3,228 times the force of gravity, at the second release speed of 6200 rpm. The total release force necessary to activate the second release valve is calculated as described above for the metering member 70.

The second release valve 58 is identical to the first release valve 74 except that the second release valve does not have the peripheral skirt 164, and thus has a lower combined mass of 0.065 gm (valve and fluid head) with identical geometry. This valve is at a radial distance of approximately 8.4 cm from the axis 26 of the rotor 24, and is engineered to release the fluid contents of the second reaction section 56 at a rotational speed of approximately 7,400 rpm. The sealant area for the second valve is the same as for the first valve (0.167 cm$^2$). As stated above, the center of mass of the second valve is positioned at approximately 8.4 cm from the center of rotation, which will apply a force of 5,100 Gs at the rotational speed of 7,400 rpm to release the second valve and the contents of the second reactant section into the photometric analysis section 58. Alternately the mass of the second release valve can be increased and the ratio of Uniflex to mineral oil can be raised to 90.2% to 9.8% for the same yield strength of 982 dynes/cm$^2$.

Figure 11A:
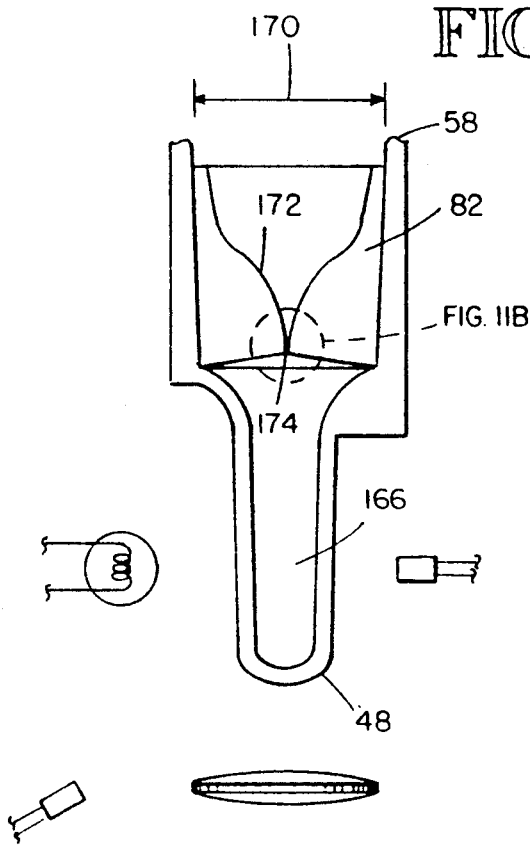
FIG. 11A is an enlarged, sectional view of a photometric detection chamber shown in FIG. 2A.
Figure 11B:
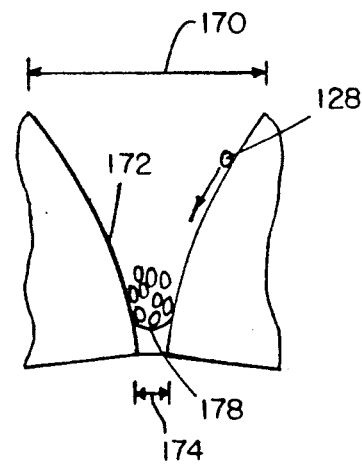
FIG. 11B is an enlarged, sectional view of circled area 11B shown in FIG. 11A.

The photometric analysis chamber is best seen in FIGS. 11A and 11B. For certain biological assays, the photometric analysis section 58 is filled with a plurality of immiscible fluid layers which have specific densities different from the fluid released from the second reactant section. The interface ,between these fluids forms a surface tension barrier which must be penetrated by the enzyme conjugate which is attached to bromostyrene latex spheres having a specific gravity of approximately 1.45 and a diameter of approximately one micrometer. At approximately 4,000 rpm, at a radial distance of approximately 3.5", a concentration of only approximately 100,000 spheres would be needed to form a sufficient "mass" to be driven through the interface between the two fluids.

With the preferred embodiments, the accumulator 82 serves to collect spheres in a vertical array having a sufficient height so the total mass of 60 to 120 million spheres is presented to the interface. The accumulator 82 comprises a disc having a diameter 170 slightly smaller than the inner diameter (approximately 0.402") of the photometric analysis section 58. The disc defines a funnel having a substantially exponential taper which ends in a small diameter (maximum diameter 0.001" to 0.30") aperture. As shown in FIG. 11B, a wash liquid 166 fills the photometric analysis section 58 such that the upper level 178 is located adjacent to the smallest diameter 174 of the funnel 172. The steep slope of the funnel wall, combined with the exaggerated curvature of the meniscus of the fluid, forms an interface between the funnel wall and fluid meniscus with an obtuse angle. This junction does not impede the transfer of spheres 180 through the interface between the fluids and limits fluid turbulence. The spheres can thus build to a sufficient mass as described above, to penetrate the meniscus and enter the distal end 48 of the photometric section. The mass of particles allows the particles to move through fluid layers rapidly. In addition, the small aperture of the accumulator prevents the immiscible fluids from moving into any other position with various changes in orientation. This structure allows an additional aqueous solution to be placed on top of the accumulator with no possibility of being mixed with the aqueous layer sandwiched between two immiscible layers in other storage or shipping orientations. This result is accomplished because of the surface tension and capillary forces formed by the immiscible fluid and the geometry of the accumulator.

The above described reaction cartridge 20, in each of the preferred, alternate embodiments, provides a simple structure for performing precise sample metering and sequential reactant mixing in an economical structure.

The seals in the junction between the metering member 70 and force sensitive release valves 74 and 78 and the surrounding seal surfaces are formed by temporarily fixing the moveable member, with respect to their surrounding sealing surfaces so as to minimize the gap distance therebetween, heating the structures to approximately 85 degrees C., and introducing a small amount of melted (85 degrees C.) sealant into the gaps formed therebetween. The melted sealant will flow into the gaps through capillary action and surface tension.

The parts are maintained in their respective positions until the sealant and parts cool to room temperature, in an assembly jig (not shown) or the like, as will be well understood to those of ordinary skill in the art.

The release of the seals is controlled exclusively by the ratio of Ultraflex sealant to mineral oil, the geometry of the interfacing sealing surfaces, and the mass of the moving parts. Thus, the invention is amenable to many structural variations. For example, the shear seal 150 and tension seal 152 shown in FIG. 9 can be achieved with a combined geometry in which a single interface surface is positioned at a 45 degree angle with respect to the direction of the releasing force. In this geometry, the shear and tensile forces would be divided proportionately. By changing the interface surface to be more parallel to the releasing force, the shear characteristics of the seal would dominate over the tensile characteristics. Conversely, as the seal interface structure becomes more transverse to the direction of the releasing force, the tensile characteristic of the seal would become more prominent than the shear characteristic.

The technique embodied in the description of the preferred embodiment is therefore capable of various geometric interpretations as a matter of choice for one of ordinary skill in this art.

Figure 10:
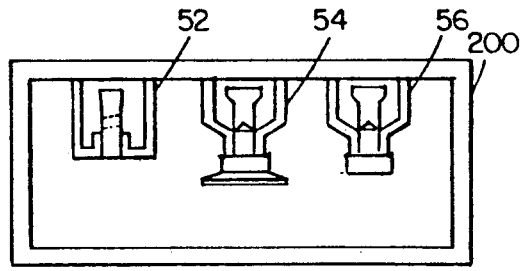
FIG. 10 is an alternate embodiment of the cartridge shown in FIG. 2A.

Furthermore, the modular nature of the aliquoting, reactant and photometric analysis sections permits various interconnections which will also be well within the ability of those of ordinary skill in the art. For example, as shown in FIG. 10, the various sections can be arranged in a parallel structure 200 where release of the metered fluid and reactants into a common reaction chamber is desired.

In view of the above, the invention is not to be limited by the above disclosure, but is to be determined in scope by the claims which follow.

We claim:
1. A centrifugal force responsive fluid metering device for use with biological assay cartridges, comprising:
   a slidable metering member having a pre-determined mass and defining a metering cavity for metering a precise quantity of analyte in a fluid, the metering member being moveable from a first collecting position through a second sealed position to a third dispensing position;
   a fluid metering chamber for slidably supporting the metering member and for containing the fluid to be metered, the metering chamber having a sealing surface slidably abutting the metering member so as to define a predetermined gap distance therebetween and having a surface area sufficiently large to completely enclose the metering cavity when the metering member is in the second sealed position and sufficiently small to permit the metering cavity to be filled with the fluid when the metering member is in the first collecting position and to permit the metering cavity to dispense the fluid therefrom when the metering member is in the third dispensing position; and
   a sealing material positioned in the gap between the metering member and the sealing surface to substantially prevent fluid communication between the first fluid collecting and third fluid dispensing positions except for the metered quantity of fluid, the sealing material having a preselected shear strength, whereby the metering member slides from the first to third positions only upon application of a first predetermined centrifugal force thereto in a predetermined direction defined by the first, second and third positions. supplemental sealing means for sealing the fluid metering chamber when the metering member is in the third fluid dispensing.

2. The metering device of claim 1, including entrapment means for preventing the metering member from escaping from the metering chamber past the third dispensing position.

3. The metering device of claim 1, wherein the metering member has a substantially elongated cylindrical body and wherein the metering cavity is located in the side of the body, wherein the sealing surface in the fluid metering chamber is a substantially cylindrical surface of larger, substantially constant diameter than the metering member body so that the gap is annular and positioned so that the metering body and sealing surface define an axis aligned with the predetermined direction.

4. The metering device of claim 3 wherein the metering member includes an enlargement on one end thereof of seal the bore when the metering member enters the third dispensing position, thereby sealing the fluid metering chamber.

5. The metering device of claim 3, wherein the metering chamber is a substantially hemispherical divot.

6. The metering device of claim 3, wherein the sealing material is sufficiently compliant so as to reseal itself after shearing, and wherein the seal material has a lower sheer strength than adhesive strength.

7. The metering device of claim 6, wherein the gap distance is approximately 0.0025", wherein the area of the sealing surface abutting the metering member is approximately 1.183 cm$^2$, wherein the shear strength of the sealing material in the gap is approximately 382 dynes/cm$^2$, and wherein the metering member and the fluid to be contained in the metering cavity have a combined mass of approximately 0.34 gm, whereby the metering member will slide from the first fluid collecting to third fluid dispensing position upon application of a force of approximately 1454 gravities in the predetermined direction.

8. The metering device of claim 1, adapted so as to be useful for metering a precise volume of plasma from a whole blood sample introduced into the metering chamber including, a peripheral blood cell sump located in the metering chamber below the metering cavity in the direction of the predetermined centrifugal force, wherein the metering member is a cylindrical metering body and wherein the metering cavity is a transverse bore passing through the cylindrical metering body at an oblique angle with respect to the axis of the cylindrical metering body, whereby whole blood cells in the metering chamber and in the metering cavity will collect in the blood cell sump upon application of a centrifugal force in the axial direction leaving only blood plasma in the metering chamber to be disposed upon application of the predetermined centrifugal force.

9. The metering device of claim 1, including a first reaction chamber for containing a first reaction fluid, connected to and positioned axially with respect to the metering chamber so as to receive metered analyte dispensed therefrom, the reaction chamber having a centrifugal force-sensitive release valve therein including release means for opening the release valve at a second predetermined centrifugal force greater than the first predetermined centrifugal force.

10. The metering device of claim 9, wherein the centrifugal force-sensitive release valve has a cylindrical valve body having a preselected mass and is reciprocally moveable between open and closed positions in an axially directed bore defined by the reaction chamber, including a sealing material having a second preselected shear strength in an annular gap formed between the cylindrical valve body and the bore, whereby the centrifugal force-sensitive release valve will open and release the contents of the reaction chamber upon application of the second predetermined centrifugal force.

11. The metering device of claim 10, wherein the centrifugal force-sensitive release valve includes a tensile release structure having a radially directed sealing surface extending from the bore, a radially extending foot connected to the cylindrical valve body, and a sealing material having a preselected tensile strength between the radially directed sealing surface and the foot.

12. The metering device of claim 11, wherein the radially extending foot has a peripheral, frusto-conic skirt extending therefrom to distribute the contents of the first reaction chamber in a radially outward direction.

13. The metering device of claim 9, including a second reaction chamber for containing a second reaction fluid, connected to and connected axially with respect to the first reaction chamber so as to receive reacted analyte dispensed from the first reaction chamber, the second reaction chamber having a centrifugal force-sensitive release valve therein including release means for opening the release valve at a third predetermined centrifugal force greater than the first and second predetermined centrifugal force.

14. The metering device of claim 1, including a photometric analysis chamber connected to the metering chamber so as to receive metered analyte therefrom for photometric analysis in a fluid contained in the photometric analysis chamber, the photometric analysis chamber further including accumulation means for concentrating the population density of particles above a fluid interface in the photometric analysis chamber to facilitate the movement of the particles across a fluid meniscus formed at the fluid interface by centrifugal force.

15. The metering device of claim 1 including a second metering device connected in series therewith.

16. The metering device of claim 1, including supplemental sealing means for sealing the fluid metering chamber when the metering member is in the third fluid dispensing position.

17. A force responsive fluid metering cassette for performing biological assays and chemical reactions, comprising:
a metering chamber having means for accepting a fluid to be metered and means for precisely metering a portion of the fluid upon application of a first centrifugal force;
a first reaction chamber for containing a first reaction fluid, the reaction chamber being connected to the metering chamber and having means for receiving the metered fluid therefrom and means for releasing the contents of the reaction chamber upon application of a second predetermined centrifugal force greater than the first centrifugal force; and
a photometric analysis chamber connected to the first reaction chamber so as to receive the contents of the first reaction chamber therefrom for photometric analysis in a fluid contained in the photometric analysis chamber, the photometric analysis chamber further including accumulation means for concentrating the population density of particles above a fluid interface in the photometric analysis chamber to facilitate the movement of the particles across a fluid meniscus formed at the fluid interface by centrifugal force.

18. The metering device of claim 17, including a second reaction chamber for containing a second reaction fluid, connected between the first reaction chamber and the photometric analysis chamber so as to receive fluid dispensed from the first reaction chamber, the second reaction chamber having means for releasing the contents of the second reaction into the photometric analysis chamber upon application of a third predetermined centrifugal force, greater than the first and second centrifugal forces.

19. An acceleration responsive fluid metering cassette for performing biological assays and chemical reactions, comprising:
an enclosed reaction chamber having means for making a photometric determination of the contents therein;
a metering chamber within the reaction chamber, the metering chamber having means for accepting a fluid to be metered and means for precisely metering a portion of the fluid into the reaction chamber upon application of a first centrifugal force;
a first reaction fluid container in the reaction chamber for containing a first reaction fluid, the reaction fluid container having means for releasing the first reaction fluid upon application of a second predetermined centrifugal force greater than the first centrifugal force.

20. The metering device of claim 19, including a second fluid reaction container in the reaction chamber for containing a second reaction fluid, the second reaction fluid into the reaction chamber upon application of a third predetermined acceleration, greater than the first and second accelerations, by centrifugal force.

21. A centrifugal force-sensitive release valve, comprising:
- a movable member having a predetermined mass and a sealing surface thereon;
- a fixed member having an aperture therein sized to slidably receive the fixed member so as to form a peripheral gap therebetween in the approximate range of 0.002" to 0.020"; and
- a sealing material in the peripheral gap having a preselected strength, whereby application of a predetermined force on the moveable member will shear the sealing material and allow the moveable member to move.

* * * * *

UNITED STATES PATENT AND TRADEMARK OFFICE
CERTIFICATE OF CORRECTION

PATENT NO. : 5,171,533
DATED : December 15, 1992
INVENTOR(S) : Richard A. Fine et al.

It is certified that error appears in the above-identified patent and that said Letters Patent is hereby corrected as shown below:

In column 14, claim one, lines 35 through 38, please delete "supplemental sealing means for sealing the fluid metering chamber when the metering member is in the third fluid dispensing".

In column 14, claim four, line 54, please delete "of" and substitute therefor --to--.

In column 15, claim eight, line 21, please delete "disposed" and substitute therefor --dispensed--.

Signed and Sealed this

Thirtieth Day of November, 1993

Attest:

BRUCE LEHMAN

Attesting Officer

Commissioner of Patents and Trademarks